US012588878B2

(12) United States Patent
    Takahashi

(10) Patent No.:  US 12,588,878 B2
(45) Date of Patent:      Mar. 31, 2026

(54) X-RAY DETECTOR AND RADIOGRAPHIC X-RAY APPARATUS

(71) Applicant: Sharp Display Technology Corporation, Kameyama City (JP)

(72) Inventor: Kozo Takahashi, Kameyama City (JP)

(73) Assignee: Sharp Display Technology Corporation, Kameyama City (JP)

( * ) Notice: Subject to any disclaimer, the term of this patent is extended or adjusted under 35 U.S.C. 154(b) by 140 days.

(21) Appl. No.: 18/604,646

(22) Filed: Mar. 14, 2024

(65) Prior Publication Data

US 2024/0353581 A1      Oct. 24, 2024

(30) Foreign Application Priority Data

Apr. 19, 2023      (JP) ................................. 2023-068668

(51) Int. Cl.
    *G01T 1/20*        (2006.01)
    *A61B 6/42*        (2024.01)

(52) U.S. Cl.
    CPC .......... *A61B 6/4233* (2013.01); *G01T 1/2002* (2013.01); *G01T 1/20185* (2020.05)

(58) Field of Classification Search
    CPC ... A61B 6/4233; G01T 1/2002; G01T 1/2006; G01T 1/20185; G01N 2223/1016; G01N 2223/505
    See application file for complete search history.

(56) References Cited

U.S. PATENT DOCUMENTS

| | | | | |
|---|---|---|---|---|
| 6,528,796 | B1 * | 3/2003 | Kaifu | .................... G01T 1/2006 |
| | | | | 250/370.11 |
| 9,006,665 | B2 * | 4/2015 | Nagano | ................. G01T 1/2002 |
| | | | | 250/363.01 |
| 9,072,451 | B2 * | 7/2015 | Benlloch Baviera | .. A61B 6/037 |
| 9,575,190 | B2 * | 2/2017 | Wu | ..................... G01T 1/20185 |
| 2012/0136237 | A1 * | 5/2012 | Benlloch Baviera | ........................ |
| | | | | A61B 5/0035 |
| | | | | 600/411 |

(Continued)

FOREIGN PATENT DOCUMENTS

| | | |
|---|---|---|
| JP | 2006162293 A | 6/2006 |
| JP | 2009-222578 A | 10/2009 |

OTHER PUBLICATIONS

English translation of JP 2006-162293 A (original cited in the IDS filed Oct. 2, 2024) (Year: 2006).*

(Continued)

*Primary Examiner* — Thomas R Artman
(74) *Attorney, Agent, or Firm* — ScienBiziP, P.C.

(57)                ABSTRACT

An X-ray detector includes a plurality of scintillators each configured to convert incident X-rays into light and emit the light, a plurality of low refractive layers that are alternately stacked with the plurality of scintillators and that have a refractive index lower than the scintillators, and a photoelectric conversion element array including a plurality of arrayed photoelectric conversion elements each configured to convert the light emitted from the alternately stacked scintillators and low refractive layers into an electrical signal. At least one of the scintillator and the low refractive layer includes a light collecting portion that focuses the emitted light toward a corresponding one of the photoelectric conversion elements.

5 Claims, 5 Drawing Sheets

(56)     References Cited

U.S. PATENT DOCUMENTS

| 2013/0134312 A1* | 5/2013 | Nagano ................. G01T 1/2002 |
| | | 250/361 R |
| 2014/0145085 A1* | 5/2014 | Wu ..................... G01T 1/20185 |
| | | 250/366 |
| 2020/0132866 A1* | 4/2020 | Taherion ................... G01T 1/20 |
| 2024/0353581 A1* | 10/2024 | Takahashi .............. G01N 23/04 |

OTHER PUBLICATIONS

English translation of JP 2009-222578 A (original cited in the IDS filed Mar. 14, 2024) (Year: 2009).*

* cited by examiner

X-RAY DETECTOR AND RADIOGRAPHIC X-RAY APPARATUS

BACKGROUND

1. Field

The present disclosure relates to an X-ray detector and a radiographic X-ray apparatus.

2. Description of the Related Art

X-ray detectors have been developed that irradiate an object, such as the human body, with X-rays and detect the transmitted X-rays. Such X-ray detectors are used in radiographic X-ray apparatuses for diagnostic imaging and the like. The X-ray detector used in a radiographic X-ray apparatus detects the X-ray intensity as an electrical signal by using a scintillator that converts X-rays into visible light and a photoelectric conversion element array including a plurality of photoelectric conversion elements that convert visible light emitted from the scintillator into an electrical signal.

As a technique for increasing the resolution of images obtained from such an X-ray detector, Japanese Unexamined Patent Application Publication No. 2009-222578 describes an X-ray solid-state detector including a scintillator and a photoelectric conversion element array. The scintillator converts X-rays incident on the first principal surface into light with a longer wavelength than that of the X-rays and emits the light from the second principal surface opposite the first principal surface. The scintillator has a condenser lens shape on at least one of the first principal surface and the second principal surface, and the photoelectric conversion element array is provided adjacent to the second principal surface and includes photoelectric conversion elements each converting the light into an electrical signal.

However, in some configurations of the above noted existing X-ray solid-state detectors, if the refraction or scattering of light is too high inside (in the upper portion) of the scintillator, it may be difficult for the surface having a condenser lens shape to fully collect the light. In this case, the edge of an object may not change in luminance in a step-like manner, but may change in a gradient-like manner. This may cause blurring of the image. Therefore, an X-ray detector and a radiographic X-ray apparatus capable of capturing images with reduced blurring are desired.

SUMMARY

According to an embodiment of the present disclosure, an X-ray detector includes a plurality of scintillators each configured to convert incident X-rays into light and emit the light, a plurality of low refractive layers that are alternately stacked with the plurality of scintillators and that have a refractive index lower than the scintillators, and a photoelectric conversion element array including a plurality of arrayed photoelectric conversion elements each configured to convert the light emitted from the alternately stacked scintillators and low refractive layers into an electrical signal. At least one of the scintillator and the low refractive layer includes a light collecting portion that focuses the emitted light toward a corresponding one of the photoelectric conversion elements.

DESCRIPTION OF THE EMBODIMENTS

Figure 1:
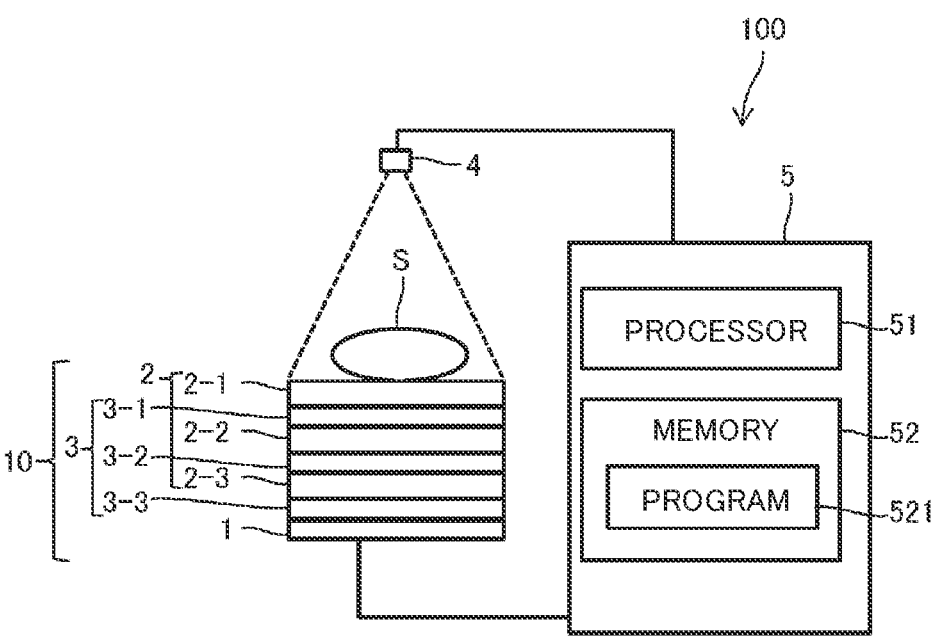
FIG. 1 is a schematic illustration of the configuration of a radiographic X-ray apparatus according to a first embodiment.

1. Overview of X-Ray Detector and Radiographic X-Ray Apparatus (1) An X-ray detector according to an embodiment includes a plurality of scintillators each configured to convert incident X-rays into light and emit the light, a plurality of low refractive layers that are alternately stacked with the plurality of scintillators and that have a refractive index lower than the scintillators, and a photoelectric conversion element array including a plurality of arrayed photoelectric conversion elements each configured to convert the light emitted from the alternately stacked scintillators and low refractive layers into an electrical signal. At least one of the scintillator and the low refractive layer includes a light collecting portion that focuses the emitted light toward a corresponding one of the photoelectric conversion elements.

The plurality of stacked scintillators can provide more reduction in light refraction and scattering than a single scintillator having a thickness equal to the sum of the thicknesses of the plurality of scintillators.

The plurality of scintillators and the plurality of low refractive layers are alternately stacked on top of each other, and at least one of the scintillator and the low refractive layer has a light collecting portion, so that the light refracted or scattered in each of the scintillators is focused toward the corresponding photoelectric conversion element by the light collecting portion. At this time, since the refraction and scattering of light in one scintillator is low, the light is precisely collected by each of the light collecting portions. As a result, a radiographic X-ray apparatus having the X-ray detector mounted therein can capture an image with reduced blurring.

(2) In the X-ray detector described in configuration (1), the light collecting portion may be a boundary surface of the scintillator bounded by the low refractive layer, and the boundary surface may have a convex lens shape that is convex in an emission direction. As a result, the light is focused toward the corresponding photoelectric conversion element in the light collecting portion of each of the scintillators.

(3) In the X-ray detector described in configuration (1) or (2), the light collecting portion may be a convex lens-shaped portion of the low refractive layer that is convex in an incident direction. As a result, the light is focused toward the corresponding photoelectric conversion element in the light collecting portion of each of the scintillators.

(4) The X-ray detector described in any one of configurations (1) to (3) may further include a semireflecting layer stacked on the incident side of the scintillator and configured to reflect light incident on a first surface adjacent to the scintillator and transmit light incident on a second surface opposite the first surface. The semireflecting layer reflects light scattered in a direction toward the opposite side of the photoelectric conversion element array in the scintillator. Consequently, the light scattered in the direction toward the opposite side of the photoelectric conversion element array is again incident on the scintillator and is emitted from the scintillator toward the photoelectric conversion element array. As a result, the detection sensitivity of the X-ray detector can be increased.

(5) In the X-ray detector described in any one of configurations (1) to (4), the thickness of the scintillator may be selected such that a distance from an incident position of the X-ray on the scintillator to an emission position of the light in an array direction of the photoelectric conversion elements is less than or equal to the length of the photoelectric conversion element in the array direction. Consequently, diffusion of light by each of the scintillators is reduced so as to be within the corresponding photoelectric conversion element and does not reach adjacent photoelectric conversion elements. As a result, diffusion of light by the scintillator is reduced in a radiographic X-ray apparatus having the X-ray detector mounted therein.

(6) A radiographic X-ray apparatus according to an embodiment includes the X-ray detector described in any one of configurations (1) to (5). This reduces refraction and scattering of light by the scintillator, and the radiographic X-ray apparatus can capture an image with reduced blurring.

2. Examples of X-Ray Detector and Radiographic X-Ray Apparatus

First Embodiment

Configuration of X-Ray Radiography Apparatus

FIG. 1 is a schematic illustration of the configuration of a radiographic X-ray apparatus 100 according to the first embodiment. The radiographic X-ray apparatus 100 includes an X-ray detector 10 and a light source 4. The radiographic X-ray apparatus 100 further includes a control unit 5 connected to the X-ray detector 10 and the light source 4. The control unit 5 includes a processor 51 and a memory 52. The control unit 5 is connected to an operation unit (not illustrated). The processor 51 executes a program 521 stored in the memory 52 in accordance with a user operation to control the irradiation of X-rays by the light source 4 and capturing of an image performed by the X-ray detector 10.

The light source 4 emits X-rays under the control of a controller of the control unit 5. When an object S is located in the irradiation direction of the X-rays, the X-rays emitted from the light source 4 are transmitted through the object S. The X-rays that have been transmitted through the object S are incident on the X-ray detector 10.

The X-ray detector 10 includes a photoelectric conversion element array 1 and a plurality of scintillators 2-1, 2-2, and 2-3 disposed closer to the light source 4 than the photoelectric conversion element array 1. The plurality of scintillators 2-1, 2-2, and 2-3 are collectively referred to as "scintillators 2". In the following description, the side adjacent to light source 4 is also referred to as an upper level, and the opposite side, that is, the side adjacent to the photoelectric conversion element array 1 is also referred to as a lower level. The scintillators 2-1, 2-2, and 2-3 are stacked in this order from the upper level.

The scintillator 2 is made of a material that is appropriate for the X-rays to be detected. The material of scintillator 2 is, for example, a single-crystal or polycrystalline material, such as Tl:CsI (thallium activated cesium iodide) or GOS (gadolinium oxysulfide). Therefore, the refractive index n1 of the scintillator 2 is about 1.8 to about 2.5.

The scintillator 2 converts incident X-rays into light and emits the light. The scintillator 2 converts the X-rays into light with a longer wavelength than X-rays. The scintillator 2 converts the X-rays into fluorescence, ultraviolet light, visible light, or infrared light, for example. Hereinafter, the light emitted from the scintillator 2 is also referred to as "scintillation light".

The X-ray detector 10 further includes a plurality of low refractive layers 3-1, 3-2, and 3-3. The low refractive layers 3-1, 3-2, and 3-3 are stacked in this order from the upper level. The plurality of low refractive layers 3-1, 3-2, and 3-3 are collectively referred to as "low refractive layers 3".

The X-ray detector 10 has a structure in which the plurality of layers of the scintillators 2 and the plurality of low refractive layers 3 are repeatedly stacked. That is, the low refractive layers 3 and the scintillators 2 are alternately stacked on top of each other. More specifically, the plurality of low refractive layers 3-1, 3-2, and 3-3 are stacked at the lower level than the plurality of scintillators 2-1, 2-2, and 2-3, respectively. In the present example, the scintillator 2-1, low refractive layer 3-1, scintillator 2-2, low refractive layer 3-2, scintillator 2-3, and low refractive layer 3-3 are stacked in this order from the upper level. The repeated stacking structure is not limited to three layers, but may be two layers or four or more layers. The low refractive layer 3 may not be stacked at the lower level than every one of the scintillators 2.

The low refractive layer 3 has a lower refractive index than the scintillator 2 and has a refractive index n2 of about 1.4. The low refractive layer 3 is made of acrylic resin, for example. The low refractive layer 3 refracts the light incident from the scintillator 2 located at an upper level with a refractive index lower than that of the scintillator 2 and emits the light.

At least one of the scintillator 2 and the low refractive layer 3 has a light collecting portion. The light collecting portion focuses the scintillation light toward a corresponding one of photoelectric conversion elements 14. The term "corresponding photoelectric conversion element 14" refers to the photoelectric conversion element 14 located in the direction of X-ray irradiation from the position (the incident point) where the X-ray emitted from the light source 4 is incident on the uppermost scintillator 2-1 of the X-ray detector 10. The light collecting portion is described below.

The photoelectric conversion element array 1 is stacked on the opposite side of the stacked scintillators 2 and low refractive layer 3 from the light source 4. That is, the photoelectric conversion element array 1 is stacked on (at the lower level than) the lowermost low refractive layer 3-3 of the alternately stacked scintillators 2 and low refractive layers 3. The photoelectric conversion element array 1 functions as a sensor.

Figure 2:
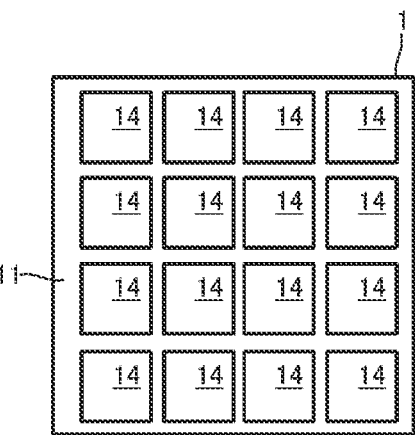
FIG. 2 is a schematic illustration of the configuration of a photoelectric conversion element array included in an X-ray detector mounted in the radiographic X-ray apparatus.

FIG. 2 is a schematic illustration of the configuration of the photoelectric conversion element array 1. The photoelectric conversion element array 1 includes the plurality of photoelectric conversion elements 14. The plurality of photoelectric conversion elements 14 are arrayed on a substrate 11 in a matrix. One photoelectric conversion element 14 corresponds to one pixel, which is the smallest unit of an image (a radiographic X-ray image).

The photoelectric conversion element array 1 includes, for example, a photodiode and a thin-film transistor (TFT). The photoelectric conversion element 14 converts scintillation light incident from the scintillator 2 through the low refractive layer 3-3 into an electric charge corresponding to the amount of light. A signal corresponding to the converted electric charge is output from the photoelectric conversion element 14 to the control unit 5 as a data signal.

Image Capturing Method for Use of Radiographic X-Ray Apparatus

The object S is placed between the light source 4 and the uppermost scintillator 2-1 of the alternately stacked scintillators 2 and low refractive layer 3 (refer to FIG. 1). X-rays are emitted from the light source 4 under the control of the control unit 5. If the object S is placed, the X-rays are emitted to the object S. The X-rays transmitted through the object S are converted into scintillation light by the scintillator 2. The scintillation light emitted from the scintillator 2 is refracted by the low refraction layer 3 and is incident on the photoelectric conversion element array 1. The photoelectric conversion element array 1 captures the incident scintillation light under the control of the control unit 5. The control unit 5 generates a radiographic X-ray image based on a data signal output from the photoelectric conversion element array 1. As an example, the processor 51 sets the pixel value in accordance with the voltage value of the data signal for each of the pixels.

Configuration of X-ray Detector

Figure 3:
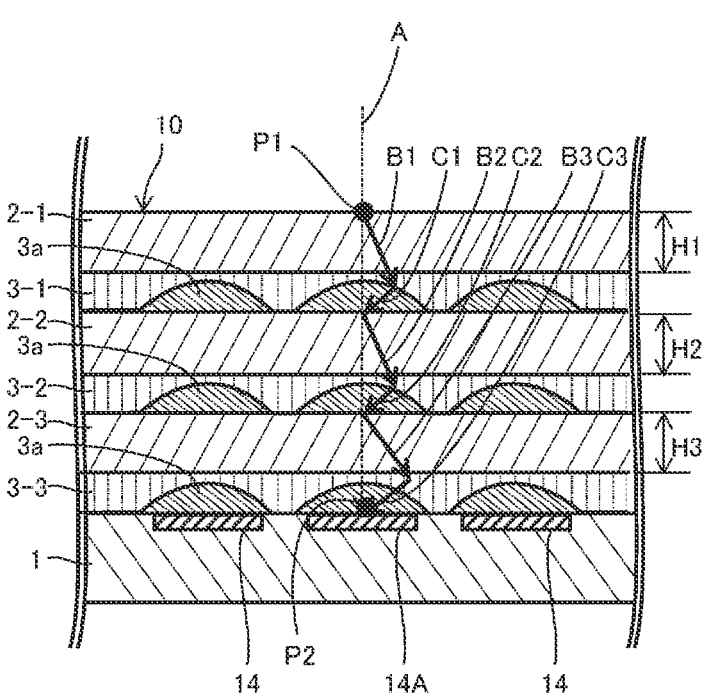
FIG. 3 is a schematic cross-sectional view of the X-ray detector according to the first embodiment.

FIG. 3 is a schematic cross-sectional view of the X-ray detector 10 according to the first embodiment. In the X-ray detector 10 according to the first embodiment, the low refractive layer 3 has a light collecting portion 3*a*. The light collecting portion 3*a* is, for example, a convex lens-shaped portion that is convex toward the scintillator 2 stacked at the upper level. The light collecting portion 3*a* is made of, for example, acrylic resin. The refractive index of the light collecting portion 3*a* is higher than that of the portion of the low refractive layer 3 other than the light collecting portion 3*a*. The refractive index of the light collecting portion 3*a* is, for example, about 1.5. For example, the light collecting portion 3*a* is disposed at the upper level of each of the plurality of photoelectric conversion elements 14 arrayed in the photoelectric conversion element array 1.

X-rays A emitted from the light source 4 is incident on the uppermost scintillator 2-1 of the X-ray detector 10 at an incident point P1 located on the upper surface of the scintillator 2-1. The X-ray A incident from the incident point P1 is converted into scintillation light B1 in the scintillator 2-1. The scintillation light B1 is refracted according to the refractive index n1 in the scintillator 2-1 and is incident on the lower-level low refractive layer 3. Some of the X-rays A incident on the scintillator 2-1 are not converted and are incident on the low refractive layer 3.

The scintillation light B1 incident from the scintillator 2-1 is refracted by the light collecting portion 3*a* of the low refractive layer 3-1 (scintillation light C1). As a result, the scintillation light C1 is incident on the lower-level scintillator 2-2 in the direction toward a photoelectric conversion element 14A.

The X-rays A that are not converted in the scintillator 2-1 are converted into scintillation light in the scintillator 2-2. The converted scintillation light, together with the scintillation light C1 incident from the low refractive layer 3-1, is refracted according to the refractive index n1 as scintillation light B2 and is incident on the low refractive layer 3-2. The scintillation light B2 is refracted by the light collecting portion 3*a* of the low refractive layer 3-2 (scintillation light C2). As a result, the scintillation light C2 is incident on the lower-level scintillator 2-3 in the direction toward the photoelectric conversion element 14A.

The X-rays A that are not converted in the scintillators 2-1 and 2-2 are converted into scintillation light in the scintillator 2-3. The converted scintillation light, together with the scintillation light C2 incident from the low refractive layer 3-2, is refracted according to the refractive index n1 as scintillation light B3 and is incident on the low refractive layer 3-3. The scintillation light B3 is refracted by the light collecting portion 3*a* of the low refractive layer 3-3 (scintillation light C3). As a result, the scintillation light C3 is incident on the photoelectric conversion element 14A.

Effect of Embodiment

The X-ray detector 10 has a structure in which the plurality of layers of scintillators 2 and the plurality of low refractive layers 3 are repeatedly stacked. The plurality of stacked scintillators 2 can provide more reduction in refraction and scattering of the scintillation light than a single scintillator having a thickness equal to the sum of the thicknesses of the plurality of scintillators 2.

Figure 4:
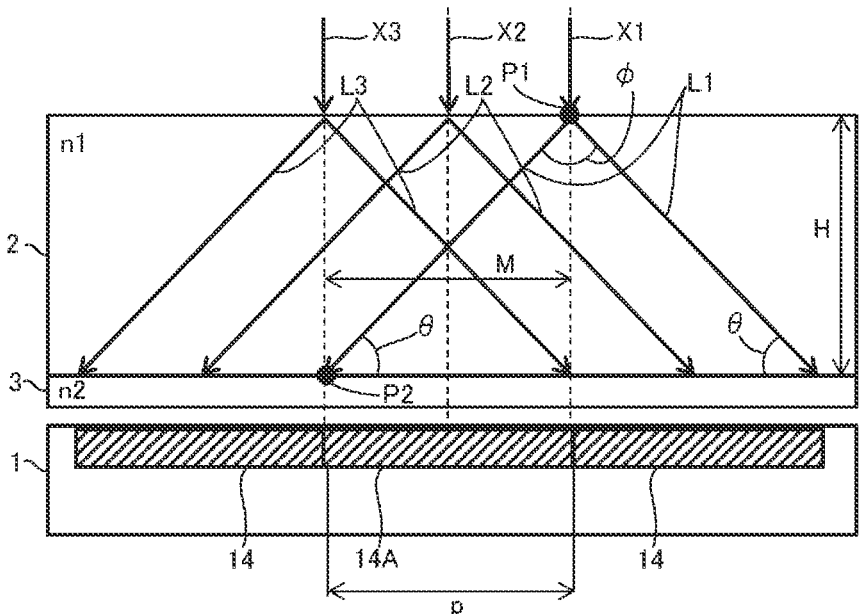
FIG. 4 illustrates the layer thickness of a scintillator included in the X-ray detector.

In the X-ray detector 10 according to the first embodiment, each of the low refractive layers 3 has the light collecting portion 3*a*, so that for each of the scintillators 2, the refracted and scattered scintillation light is focused in the light collecting portion 3*a* of the low refractive layer 3 stacked at the lower level in the direction toward the photoelectric conversion element 14A. At this time, since the refraction and scattering of the scintillation light in one scintillator 2 is low, the light is precisely collected by each of the light collecting portions 3*a*. As a result, the radiographic X-ray apparatus 100 having the X-ray detector 10 mounted therein can capture an image with reduced blurring. Modification FIG. 4 illustrates a layer thickness H of the scintillator 2. FIG. 4 indicates that the X-rays X1, X2, and X3 are incident on any one scintillator 2 among the scintillators 2-1, 2-2, and 2-3 and are converted to scintillation light. Scintillation light L1, L2, and L3 represent the maximum diffused scintillation light among the scintillation light converted from X-rays X1, X2, and X3, respectively. When the X-ray X1 is discussed, the X-ray X1 is incident on the scintillator 2 at the point P1 (the incident point P1), and the maximum diffused scintillation light L1 is emitted from a point P2 (an emission point P2).

It is desirable that the layer thickness H of each of the scintillators 2 be set so that a distance M from the incident point P1 to the emission point P2 in the array direction of the photoelectric conversion elements 14 is less than or equal to a length p (hereinafter also referred to as a "pixel pitch") of the photoelectric conversion element 14 in the array direction (M≤p).

The distance M is obtained by the equation M=H/tan θ, where θ represents the critical angle of the scintillation light of scintillator 2 at the boundary with the low refractive layer 3, and H represents the layer thickness. The critical angle θ can be obtained by the equation θ=arcsin (n2/n1). Therefore, for the layer thickness H, it is desirable that H≤p×tan θ.

For example, if the refractive index n1 of scintillator 2 is 1.8 (n1=1.8) and the refractive index n2 of low refractive layer 3 is 1 (n2=1), the critical angle θ=arcsin (1/1.8)=33.7 degrees. If the pixel pitch p is 140 μm, it is desirable that the layer thickness H of each of the scintillators 2-1, 2-2, and 2-3 be less than or equal to 93.4 μm (=140×tan (33.7)). In addition, for example, if the refractive index n1 of scintillator 2 is 1.8 (n1=1.8) and the refractive index n2 of low refractive layer 3 is 1.4 (n2=1.4), the critical angle θ is θ=arcsin (1.4/1.8)=51.1 degrees. If the pixel pitch p is 140 μm, it is desirable that the layer thickness H of each of the scintillators 2-1, 2-2, and 2-3 be less than or equal to 173.5 μm (=140×tan (51.1)).

Among the scintillation light rays that are converted from the X-ray X1 and are diffused, the scintillation light ray incident on the boundary surface with the low refractive layer 3 at a critical angle θ or less is totally reflected at the boundary surface. Therefore, a distance L from the incident point P1 to the emission point P2 of the scintillation light L1 in the array direction of the photoelectric conversion elements 14 is at most the distance to the adjacent photoelectric conversion element 14, and the scintillation light L1 does not reach the adjacent photoelectric conversion element 14. For this reason, if the layer thickness H of each of the scintillators 2-1, 2-2, and 2-3 in the X-ray detector 10 satisfies H≤p×tan θ, the diffusion of light occurs only within the corresponding photoelectric conversion element 14A in each of the scintillators 2-1, 2-2, and 2-3. As a result, in the radiographic X-ray apparatus 100 having the X-ray detector 10 mounted therein, light diffusion by the scintillator 2 is reduced, and the light is focused on the corresponding photoelectric conversion element 14A. Thus, the radiographic X-ray apparatus 100 can capture an image with reduced blurring.

Modification

Figure 5:
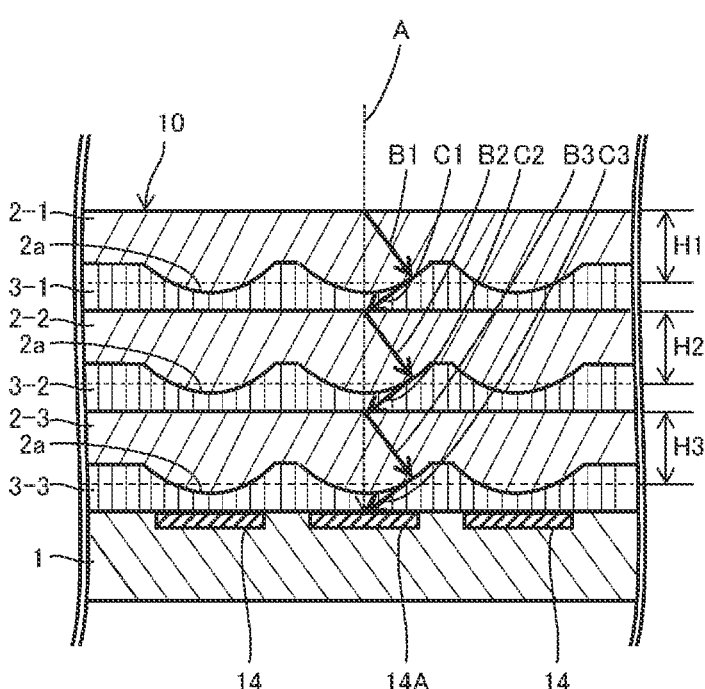
FIG. 5 is a schematic cross-sectional view of an X-ray detector according to a modification.

FIG. 5 is a schematic cross-sectional view of an X-ray detector 10 according to a modification. In the X-ray detector 10 according to the modification, the scintillator 2 includes a light collecting portion 2a. The light collecting portion 2a is a convex lens-shaped portion that is convex toward the low refractive layer 3 stacked at the lower level. For example, the light collecting portion 2a is provided on the boundary surface of the scintillator 2 with the low refractive layer 3.

In the X-ray detector 10 according to the modification, an X-ray A incident at the incident point P1 is converted into scintillation light B1 in the scintillator 2-1 and is refracted according to the refractive index n1. In the light collecting portion 2a, the scintillation light B1 is focused in the direction toward the photoelectric conversion element 14A and is incident on the lower-level low refractive layer 3. Similarly, the light is focused in each of the scintillator 2-2 and the scintillator 2-3.

As a result, scintillation light C3 emitted from the lowermost low refractive layer 3-3 is incident on the photoelectric conversion element 14A. That is, even when a light collecting portion is provided in the scintillator 2, the refraction and scattering of light by the scintillator 2 are reduced, and blurring of the captured image is reduced in the same way as when the light collecting portion is provided in the low refractive layer 3. The light collecting portion may be provided in both the scintillator 2 and the low refractive layer 3.

Second Embodiment

Configuration of X-Ray Detector

Figure 6:
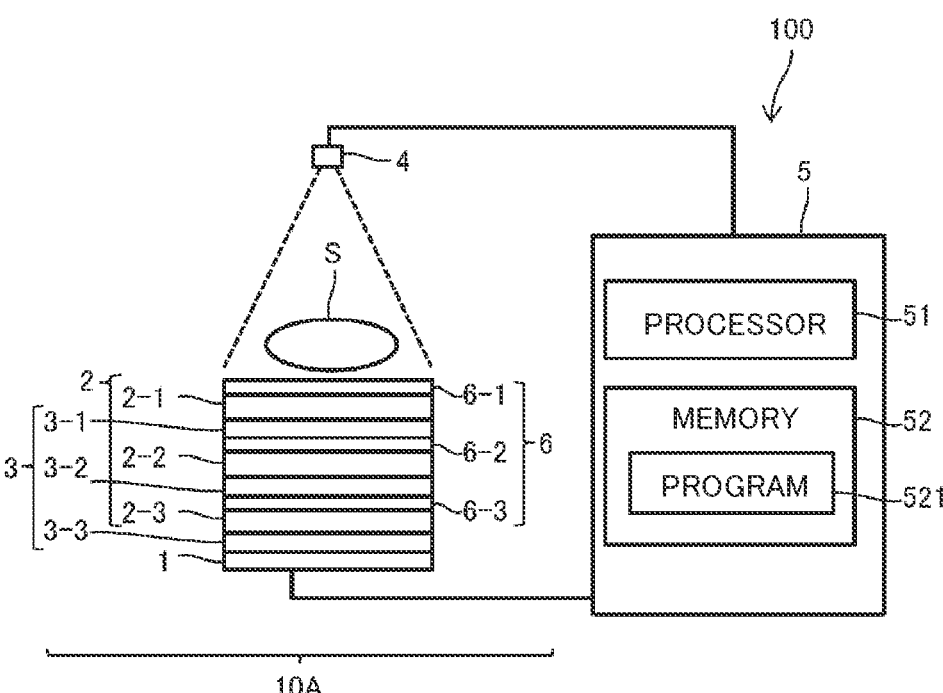
FIG. 6 is a schematic illustration of the configuration of a radiographic X-ray apparatus according to a second embodiment.
Figure 7:
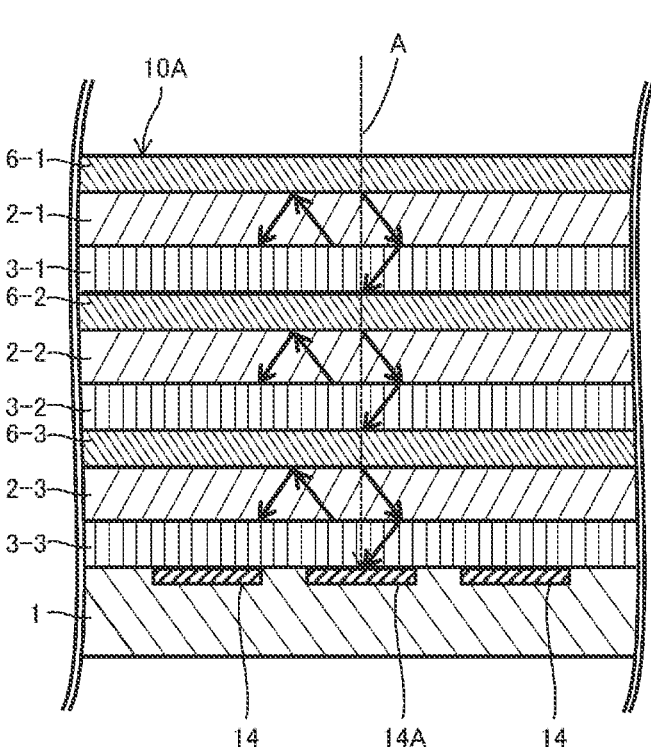
FIG. 7 is a schematic cross-sectional view of an X-ray detector according to the second embodiment.

FIG. 6 is a schematic illustration of the configuration of a radiographic X-ray apparatus 100 according to the second embodiment. The radiographic X-ray apparatus 100 according to the second embodiment includes an X-ray detector 10A instead of the X-ray detector 10. FIG. 7 is a schematic cross-sectional view of the X-ray detector 10A according to the second embodiment. In FIG. 7, the light collecting portion is not illustrated. In the X-ray detector 10A, the light collecting portion may be included in the low refractive layer 3, the scintillator 2, or both.

The X-ray detector 10A includes reflective layers 6-1, 6-2, and 6-3 stacked on the incident side of, that is, at the upper levels than a plurality of scintillators 2-1, 2-2, and 2-3, respectively. The reflective layers 6-1, 6-2, and 6-3 are collectively referred to as "reflective layers 6". The reflective layer 6 has a semireflecting (half mirror) structure that reflects light incident on a first surface is reflected and transmits light incident on a second surface opposite the first surface therethrough. In the X-ray detector 10A, the reflective layers 6-1, 6-2, and 6-3 are stacked at the upper levels than (on top of) the scintillator 2-1, 2-2, and 2-3, respectively, with the first surfaces facing the scintillators. The reflective layer 6 may have an integral structure with the low refractive layer 3.

In the X-ray detector 10A, light that is scattered in the scintillator 2 and travels in the direction toward the light source 4 is reflected by the reflective layer 6 stacked at the upper level. Therefore, the light scattered in the direction toward the light source 4 is incident on the scintillator 2 again. As a result, the light scattered in the direction from the scintillator 2 toward the light source 4 is emitted from the scintillator 2 toward the lower-level low refractive layer 3. For this reason, the detection sensitivity of the X-ray detector 10A can be increased. As a result, the radiographic X-ray apparatus 100 having the X-ray detector 10A mounted therein can obtain a high-sensitivity captured image with reduced blurring.

Third Embodiment

Configuration of X-Ray Detector

Figure 8:
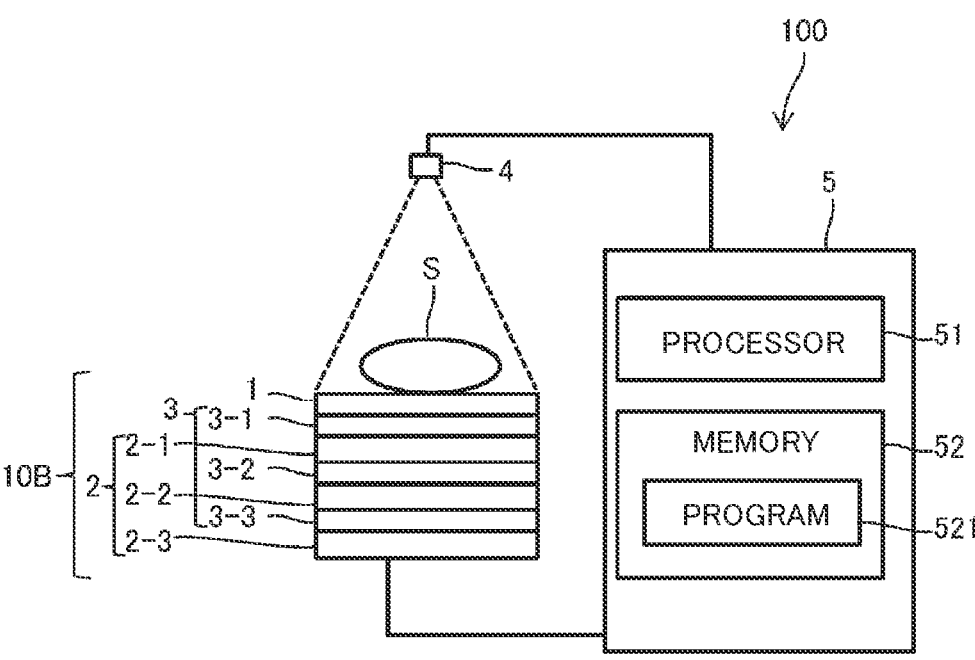
FIG. 8 is a schematic illustration of the configuration of a radiographic X-ray apparatus according to a third embodiment.
Figure 9:
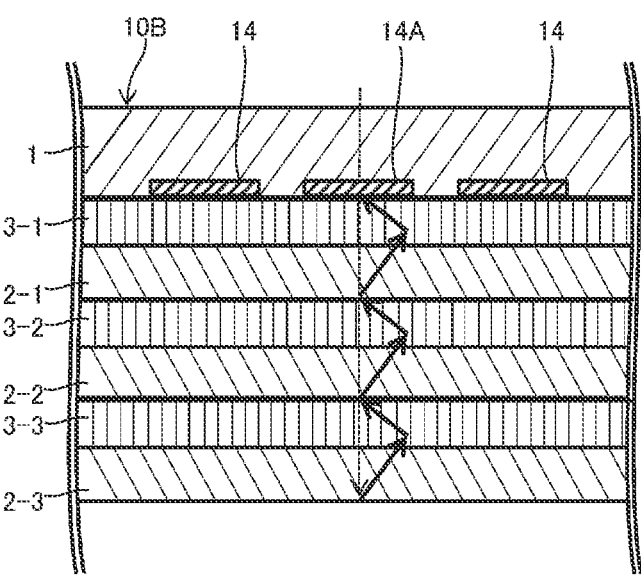
FIG. 9 is a schematic cross-sectional view of an X-ray detector according to the third embodiment.

FIG. 8 is a schematic illustration of the configuration of a radiographic X-ray apparatus 100 according to the third embodiment. The radiographic X-ray apparatus 100 according to the third embodiment includes an X-ray detector 10B instead of the X-ray detector 10. FIG. 9 is a schematic cross-sectional view of the X-ray detector 10B according to the third embodiment. In FIG. 9, a light collecting portion is not illustrated. In the X-ray detector 10B, the light collecting portion may be included in the low refractive layer 3, the scintillator 2, or both.

The photoelectric conversion element array 1 is disposed in the X-ray detector 10B at the uppermost level, and the scintillators 2 and the low refractive layers 3 are arranged at the lower level than the photoelectric conversion element array 1. The plurality of scintillators 2-1, 2-2, and 2-3 are stacked in this order, and the plurality of low refractive layers 3-1, 3-2, and 3-3 are stacked in this order from the upper level.

In X-ray detector 10B, the plurality of low refractive layers 3-1, 3-2, and 3-3 are stacked at the upper level than (on top of) the plurality of scintillators 2-1, 2-2, and 2-3, respectively. In the present example, the low refractive layer 3-1, scintillator 2-1, low refractive layer 3-2, scintillator 2-2, low refractive layer 3-3, and scintillator 2-3 are stacked in this order from the upper level.

In X-ray detector 10B, X-rays are transmitted through the object S and then through the low refractive layer 3-1 and reach the scintillator 2-1. The X-rays are converted into scintillation light in the scintillator 2-1. The scintillation light is focused by the light collecting portion and is incident on the photoelectric conversion element 14A. Some X-rays transmitted through the scintillator 2-1 are similarly converted into scintillation light in the scintillator 2-2 and scintillator 2-3, and the scintillation light is focused by the light collecting portion and is incident on the photoelectric conversion element 14A.

Therefore, even the radiographic X-ray apparatus 100 having the X-ray detector 10B mounted therein can reduce the refraction and scattering of light caused by scintillator 2 and, thus, a captured image with reduced blurring can be obtained.

3. Note

Note that the present disclosure is not limited to the above embodiments, and numerous and various modifications can be made.

The present disclosure contains subject matter related to that disclosed in Japanese Priority Patent Application JP 2023-068668 filed in the Japan Patent Office on Apr. 19, 2023, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An X-ray detector comprising:
   a plurality of scintillators, each configured to convert incident X-rays into light and emit the light;
   a plurality of low refractive layers that is alternately stacked with the plurality of scintillators and that has a refractive index lower than the plurality of scintillators;
   a photoelectric conversion element array including a plurality of arrayed photoelectric conversion elements, each configured to convert the light emitted from the plurality of scintillators and light emitted from the plurality of low refractive layers into an electrical signal; and a semi-reflecting layer, having a first surface in contact with, and adjacent to, one of the plurality of scintillators, and having a second surface opposite the first surface, uniformly stacked over an entire surface of the one of the plurality of scintillators on an X-ray incident side, the semi-reflecting layer configured to:
   reflect light obtained by converting an X-ray incident on the first surface, and
   transmit light obtained by converting an X-ray incident on the second surface,
   wherein at least one of the plurality of scintillators and the plurality of low refractive layers includes a light collecting portion that focuses the emitted lights toward a corresponding one of the plurality of arrayed photoelectric conversion elements.

2. The X-ray detector according to claim 1, wherein the light collecting portion includes a boundary surface of another one of the plurality of scintillators bounded by one of the plurality of low refractive layers, and the boundary surface has a convex lens shape that is convex in a direction toward a photoelectric conversion element.

3. The X-ray detector according to claim 1, wherein the light collecting portion is a convex lens-shaped portion of one of the plurality of low refractive layers that is convex in a direction opposite a photoelectric conversion element.

4. The X-ray detector according to claim 1, wherein a thickness of another one of the plurality of scintillators is selected such that a distance from an incident position of an X-ray on the another one of the plurality of scintillators to an emission position of the light in an array direction of the plurality of arrayed photoelectric conversion elements is less than, or equal to, a length of a photoelectric conversion element in the array direction.

5. A radiographic X-ray apparatus comprising:
   the X-ray detector according to claim 1.

* * * * *